(12) United States Patent
Kirchhofer (10) Patent No.: US 9,457,156 B2
(45) Date of Patent: Oct. 4, 2016

(54) INJECTION DEVICE COMPRISING A NEEDLE PROTECTING SLEEVE

(75) Inventor: Fritz Kirchhofer, Sumiswald (CH)

(73) Assignee: TecPharma Licensing AG, Burgdorf (CH)

(*) Notice: Subject to any disclaimer, the term of this patent is extended or adjusted under 35 U.S.C. 154(b) by 1071 days.

(21) Appl. No.: 13/495,430

(22) Filed: Jun. 13, 2012

(65) Prior Publication Data

US 2012/0316508 A1    Dec. 13, 2012

Related U.S. Application Data

(63) Continuation of application No. PCT/EP2009/067885, filed on Dec. 23, 2009.

(51) Int. Cl.
*A61M 5/32*    (2006.01)
*A61M 5/315*   (2006.01)
*A61M 5/31*    (2006.01)

(52) U.S. Cl.
CPC ........... *A61M 5/326* (2013.01); *A61M 5/3156* (2013.01); *A61M 5/3158* (2013.01); *A61M 5/31553* (2013.01); *A61M 5/3146* (2013.01); *A61M 5/3157* (2013.01); *A61M 5/31591* (2013.01); *A61M 5/3202* (2013.01); *A61M 5/3204* (2013.01); *A61M 5/3272* (2013.01); *A61M 2005/3247* (2013.01); *A61M 2005/3267* (2013.01)

(58) Field of Classification Search
CPC ............... A61M 5/326; A61M 2005/3247; A61M 2005/3267; A61M 5/3257; A61M 5/3271; A61M 5/3272
USPC .................. 604/110, 198, 187, 192
See application file for complete search history.

(56) References Cited

U.S. PATENT DOCUMENTS

| | | | | |
|---|---|---|---|---|
| 4,911,693 A | * | 3/1990 | Paris ................... | A61M 5/3271 604/192 |
| 5,681,291 A | | 10/1997 | Galli | |
| 5,688,241 A | * | 11/1997 | Asbaghi ................ | A61M 5/326 604/110 |
| 6,258,068 B1 | | 7/2001 | Kirchhofer et al. | |
| 2007/0118081 A1 | | 5/2007 | Daily et al. | |

FOREIGN PATENT DOCUMENTS

| | | |
|---|---|---|
| EP | 0956875 | 11/1999 |
| FR | 2884723 | 10/2006 |
| WO | WO 2008/025179 | 3/2008 |
| WO | WO 2008/050158 | 5/2008 |
| WO | WO 2008/077706 | 7/2008 |

* cited by examiner

*Primary Examiner* — Phillip Gray
(74) *Attorney, Agent, or Firm* — Dorsey & Whitney LLP; Stuart R. Hemphill, Esq.

(57) ABSTRACT

A device and method for protecting against needle sticks, including a needle protection sleeve for being coupled to an administering device to cover a needle associated with the administering device, wherein the sleeve can be moved against the force of a spring from an extended position to a retracted position and by the force of the spring from the retracted position to the extended position, the spring being carried on the needle protection sleeve.

20 Claims, 5 Drawing Sheets

INJECTION DEVICE COMPRISING A NEEDLE PROTECTING SLEEVE

CROSS-REFERENCE TO RELATED APPLICATIONS

This application is a Continuation of International Patent Application No. PCT/EP2009/067885 filed Dec. 23, 2009, the entire contents of which are incorporated herein by reference.

BACKGROUND

The present invention relates to devices for injecting, infusing, delivering, dispensing or administering a substance, and to methods of making and using such devices. More particularly, it relates to a device comprising a needle protecting or covering sleeve for protecting against injuries from an injection needle using which a liquid product, e.g. a drug, can be injected into a patient. In one embodiment, the invention relates to an administering device comprising a needle protecting sleeve, wherein the device is suitable for delivering a drug based on FSH or an FSH variant. The device can also be suitable for delivering neuroleptic drugs, vasodilative agents, blood products, drugs for treating rheumatic diseases, oncological drugs or drugs for treating infectious diseases. For the purpose of the present invention, "liquid drugs" is regarded as meaning not only liquids in the narrower sense but also pasty and gelatinous drugs, providing such drugs can be conveyed in a way comparable to a liquid. In some embodiments, the administering device is an injection apparatus for administering using an infusing injection needle, e.g. for a subcutaneous injection, but can in principle also be, for example, an injection apparatus for administering without a needle or an inhalation apparatus. In some preferred embodiments, an injection device in accordance with the present invention may be a so-called injection pen.

A device for administering an injectable product in doses is known from EP 0 956 875 A2 and/or U.S. Pat. No. 6,258,068. In this device, a deflector is pushed into a needle protecting sleeve counter to the force of a spring to remove the needle protecting cap, wherein an engaging element which is fastened to the deflector engages with the needle protecting cap and slaves said cap and removes it from the needle when the deflector moves out of the needle protecting sleeve in the distal direction.

SUMMARY

Any reference to "the invention" in this document shall not be construed as a generalization, limitation or characterization of any subject matter disclosed herein and shall not be considered to be an element or limitation of the appended claims except if and/or where explicitly recited in a claim(s). With regard to fastening, mounting, attaching or connecting components, unless specifically described as otherwise, conventional mechanical fasteners and methods may be used. Other appropriate fastening or attachment methods include adhesives, welding and soldering, including with regard to an electrical system, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

One object of the present invention is to provide a device and/or method for protecting against injuries from a needle, wherein the device is efficient, cost-effective to manufacture and use, and can be operated intuitively by the user.

In one embodiment, the present invention comprises a device and method for protecting against needle sticks, comprising a needle protection sleeve for being coupled to an administering device to cover a needle associated with the administering device, wherein the sleeve can be moved against the force of a spring from an extended position to a retracted position and by the force of the spring from the retracted position to the extended position, the spring being carried on the needle protection sleeve.

In one embodiment, the invention relates to a device for protection against injuries from an injection needle, comprising a housing, a needle for injecting a liquid product, and a needle protection sleeve that can be moved against the force of a spring from an extended position to a retracted position or/and by the force of the spring from the retracted position to the extended position, the spring being formed on the needle protection sleeve.

In one embodiment, the present invention involves an injection device adapted to protect against injuries, e.g. inadvertant sticks, from an injection needle, wherein the device comprises a housing, a needle through which a liquid product can be injected, and a needle protecting sleeve. The needle protecting sleeve is able to be moved counter to the force of a spring from an extended position, e.g. a needle protecting or covering position, to a retracted position, e.g. a position in which the needle is exposed for injecting, and/or is able to be moved by the force of the spring from the retracted position to the extended position. The spring exerts an energy stored in it on the needle protecting sleeve as a force acting in the distal (forward) direction, including in the initial position and/or retracted position of the needle protecting sleeve and/or the extended position or positions. In accordance with some preferred embodiments of the present invention, the spring is formed on the needle protecting sleeve, e.g. the spring and sleeve are a unitary or single part or piece. In the case of an individual spring and a needle protecting sleeve which is separate from it, two individual parts have to be integrated or inserted into the housing when the device is being assembled. Using the present invention, it is instead possible to integrate the needle protecting sleeve, including the spring, with or into the housing as a single part. This reduces manufacturing and assembling costs. Instead of two manufacturing tools or molds, only one is required, such as for example an injection-molding die for the plastic from which the needle protecting sleeve with the integrated spring is formed.

In some embodiments, the spring can be a pressure spring such as a helical spring formed at the proximal (rearward) end of the needle protecting sleeve and extending in the proximal direction. In some embodiments, the spring can also comprise a plurality of assembled bending beams, e.g. symmetrically assembled bending beams.

In some preferred embodiments, the spring is a spring arm to which a bending load or a bending moment can be applied and which then acts spring-elastically. In some embodiments, the spring arm is bent transverse to the longitudinal axis of the spring arm. In some embodiments, the spring arm can be substantially rigid and elastically deformable at substantially only one point, for example the point at which it merges onto or into the needle protecting sleeve. In one preferred example, the spring arm is elastically deformable, i.e. spring-elastic, in itself and over its entire length. The spring arm can comprise an engaging means which acts on a guiding area of a link which is inclined transverse to the longitudinal axis of the needle. The engaging means engages with the link from the inside or, alternatively, from the outside. The guiding area can be a flank of a cavity formed by the housing, e.g. a groove or pocket, which forms the link. The groove or pocket can be continuous or can comprise a groove or pocket base. The cavity is open toward the inner side or outer side of the housing. The groove or pocket can be visible from outside the device or not. The engaging means can be moved relative to the guiding area, e.g. along the guiding area and/or parallel to it. The engaging means presses against the guiding area, wherein the force applied to the needle protecting sleeve by the spring is a force component which is dependent on the inclination of the guiding area. The more significantly inclined the guiding area is in relation to the longitudinal axis of the needle, the greater the force component acting in the shifting direction of the needle protecting sleeve.

The force exerted directly by the spring can be converted, via the engagement between the engaging means and the guiding area, into an axial force which acts on the needle protecting sleeve and points and/or urges in the shifting or movement direction of the needle protecting sleeve.

In some preferred embodiments, the spring arm can project from the proximal end of the needle protecting sleeve in the proximal direction. The arm can extend along the longitudinal axis of the device or the needle protecting sleeve, for example parallel, at least when the spring arm is relaxed. The engaging means can be moved, spring-elastically, transverse to the movement direction of the needle protecting sleeve. In some preferred embodiments, the engaging means is substantially axially fixed in relation to the needle protecting sleeve in the movement direction of the needle protecting sleeve.

The needle protection or covering device in accordance with the present invention can be part of an injection device, i.e. one aspect of the present invention is an injection device into which the device for protecting against injuries from an injection needle is integrated. The housing of the injection device can correspond to the housing of the device. Alternatively, the device can be a separate unit which can be fastened to an injection device, such as for example an auto-injector or other injection device. To this end, in some embodiments, the needle protection or covering device in accordance with the present invention can, for example, comprise a housing which can be connected to the housing of the injection and/or administering device.

In some preferred embodiments, the device can comprise a housing and a needle which is preferably arranged in the longitudinal direction of the housing which is cylindrical or sleeve-shaped. The needle can be one which can be fastened to a product container, for example by a Luer lock connection, and can be a cannula. The cannula can comprise a needle support which can be connected to the container (which can also be thought of and/or referred to as an ampoule, vial or carpoule, or a carpoule holder which accommodates the carpoule. The carpoule can comprise a septum which can be pierced by the needle of the cannula when the cannula is fastened to the carpoule or the carpoule holder. At the proximal end, the drug is sealed in the carpoule by an elastic piston which abuts the inner wall of the carpoule, forming a seal, and can be shifted.

In one preferred alternative embodiment, the product container can be a syringe with a front end at which the needle is fixedly arranged. A syringe which the needle can be fastened to, for example as a cannula, is also conceivable. A syringe does not, as a general rule, comprise a septum but rather, like the carpoule, a piston. The rear end of the syringe, i.e. its proximal end, can comprise an outwardly projecting flange which is also referred to as a finger flange because it abuts against the index and middle fingers when the syringe is being manually used, while a pressure is exerted on the piston by the thumb, for example via a piston rod.

The needle for injecting the product, which may be a liquid, can optionally be covered by a needle protecting cap. The needle protecting cap predominantly serves the purpose of keeping the needle sterile and, as applicable, also protecting it against mechanical damage. The needle protecting cap is or can be fastened in a positive fit and/or a frictional fit to the needle support which can be separately fastened to the product container or is part of the product container which is designed as a syringe. The needle support can also be referred to as a fastening portion. The needle protecting cap is arranged on the needle in an initial state of the device. The needle protecting cap can for example be made of an elastic material, such as for example natural or vulcanised rubber, or can at least comprise such a material. A needle protecting sleeve designed as a composite, in which the cap is formed from the elastic material and surrounded by a plastic which is firm in relation to the cap, may also be advantageous. The needle protecting cap is then more stable and can even better protect the needle against mechanical damage. The needle protecting cap is removed from the needle before an injection.

In general terms, the needle protecting sleeve serves to protect the user against unintended needle jabs or sticks at least after and also before an injection. Since, without a needle protecting sleeve, the needle tip would be exposed after the needle has been drawn out of the body tissue, there would be a danger to third parties of injury or injection. To reduce these dangers, the needle protecting sleeve is arranged over the needle which protrudes beyond the distal (forward or front) end of the housing. The needle protecting sleeve surrounds the needle laterally. The needle protecting sleeve can protrude distally beyond the distal end of the needle, i.e. beyond the needle tip. The needle protecting sleeve can be moved, e.g. extended, relative to the housing by a movement in the distal direction, i.e. in the direction toward the needle tip. In its extended position, the needle protecting sleeve is arranged over the needle and the needle tip.

The needle protecting sleeve is able to be moved relative to the housing between an extended position, which in some preferred embodiments is the initial position of the needle protecting sleeve which it assumes in the initial or delivered state of the device, into a retracted position in which the needle protrudes beyond the distal end of the needle protecting sleeve, as for example with an injection pen for manually delivering product, or can at least be moved into a protruding position, as for example with an auto-injector in which the needle is automatically injected and the product is automatically delivered.

In some preferred embodiments, the needle protecting cap can be moved into its retracted position by pressing its distal end onto an injection point, thus enabling the needle to be injected into the body tissue. The movement of the needle protecting cap into its retracted position can cause the needle, which is fixed relative to the housing, to protrude from the needle protecting sleeve and/or can trigger an advancing mechanism, comprising for example an advancing spring, which shifts the needle in the distal direction relative to the housing, whereby the needle protrudes from the needle protecting sleeve. In the latter alternative, the needle protecting sleeve can also serve as a triggering element.

In some preferred embodiments, the needle protecting sleeve can be moved from its retracted position into an extended position by being moved in the distal (forward or injecting) direction. The extended positions before and after the movement of the needle protecting sleeve into the retracted position can be the same or different. The needle protecting sleeve can project from the distal end of the housing by different distances in different extended positions. In general terms, the needle tip is covered by the needle protecting sleeve in the extended positions. In its extended positions relative to the housing, the needle protecting sleeve is fastened to the device, e.g. to the housing of the device.

At the end of its movement from the extended position into the retracted position back into an extended position, the needle protecting sleeve is blocked against moving in the distal direction and the proximal direction. Once the device has been used, the needle protecting sleeve is advantageously latched, axially fixed, to and/or relative to the housing. The needle protecting sleeve can thus no longer be pushed back into the housing, hence the needle can no longer protrude from the distal end of the needle protecting sleeve and the danger of injury posed by the needle is reduced.

The extended position in which the needle protecting sleeve is in its initial position or moves from its initial position in the distal direction into an engagement with an abutment which acts in the proximal direction may be thought of and/or referred to as the first extended position. The position of the needle protecting sleeve in which it moves from the retracted position to the extended position and is latched, axially fixed, may be thought of and/or referred to as the second extended position. It should be appreciated the first extended position and second extended position can, but need not, be identical with regard to their position relative to the housing. The needle protecting sleeve can for example project further from the housing in the first extended position than in the second extended position, or vice versa. The needle protecting sleeve is able to be shifted counter to the force of the spring element, i.e. the spring element is tensed by shifting the needle protecting sleeve in the proximal direction, e.g. from the first extended position to the retracted position.

In some preferred embodiments, the needle protecting sleeve comprises an engaging member which engages with the housing. The engaging member, which is cam-shaped, can be mounted spring-elastically relative to the needle protecting sleeve. The spring-elastic bearing can allow a movement of the engaging member transverse to the longitudinal axis of the device or the needle protecting sleeve, wherein the engaging member cannot perform any movement or can only perform a negligible movement in the longitudinal direction of the device or the needle protecting sleeve, e.g. relative to the needle protecting sleeve. This can be achieved by an arm, one end of which is fastened in one part to the needle protecting sleeve and the other end of which comprises the engaging member. The arm can extend in the longitudinal direction of the needle protecting sleeve or the device, from the proximal end of the needle protecting sleeve in the proximal direction. The needle protecting sleeve, the arm and the engaging member may be formed in one part, such as for example a plastic part manufactured using injection-molding dies.

When the needle protecting sleeve is in its initial position or a position in which it is moved out of its initial position in the distal direction, the engaging member of the needle protecting sleeve is in engagement with an abutment which acts in the distal direction. The abutment which acts in the distal direction can also be regarded as an end abutment, since it blocks or prevents a movement of the needle protecting sleeve in the distal direction. In this position or in its initial position, the needle protecting sleeve is situated in an extended position. A movement of the needle protecting sleeve out of the extended position in the proximal direction can be possible in principle.

In some preferred embodiments, the spring-elastically arranged engaging member can be deflected by a guiding area when the needle protecting sleeve is moved out of the first extended position in the proximal direction, wherein when the needle protecting sleeve is in or has reached its retracted position, the engaging member springs back out of the deflected position. As soon as the engaging member has sprung back, the needle protecting sleeve can no longer be moved into the first extended position but rather only then into the second extended position. In some preferred embodiments, the needle protecting sleeve can only be moved into the second deflected position when the needle tip has protruded beyond the distal end of the needle protecting sleeve and/or the needle protecting sleeve has been pushed back into its retracted position, e.g. into an abutment with the housing. The engaging member can be sprung transverse to the longitudinal axis of the needle protecting sleeve, e.g. skewed with respect to the longitudinal axis.

In some preferred embodiments, the engaging member is able to be deflected by a guiding area, e.g. an additional guiding area, when the needle protecting sleeve is moved out of its retracted position in the distal direction, i.e. when it is moved into the second extended position, wherein the engaging member springs back out of the deflected position when the needle protecting sleeve is in the extended position. The engaging member is able to be deflected and to spring back transverse to the longitudinal axis, e.g. skewed.

When the needle protecting sleeve is in its second extended position, the engaging member is between an abutment which acts in the distal (forward) direction and blocks a movement of the needle protecting sleeve in the distal direction and can also be referred to as an end abutment, and an abutment which acts in the proximal (rearward) direction and blocks a movement of the needle protecting sleeve in the proximal direction. This prevents the needle protecting sleeve from moving in the distal direction and the proximal direction and latches it relative to the housing.

In some preferred embodiments, at least one and/or each of the abutments for the engaging member and/or at least one and/or each of the guiding areas for the engaging member is formed by a guiding track. The guiding track can comprise or be a guiding curve and/or a guiding straight line. In some embodiments, the guiding track is formed by the housing, and is a cavity which is open toward the inner side of the housing and which can for example be groove-shaped. The groove can be a blind groove comprising a groove base or can be a continuous groove or cavity through the wall of the housing. The continuous groove can for example be visible from the outside, wherein the blind groove can be invisible from the outside. The at least one abutment and/or the at least one guiding area can be formed by the groove base and/or groove flanks in the case of a blind groove or by the groove flanks in the case of a continuous groove. A cam-shaped engaging member engages with the guiding track, from the inner side of the housing. Alternatively, the engaging member can engage with the guiding track from the outer side of the housing, wherein the guiding track is then a cavity which is open toward the outer side of the housing. The alternative arrangement protects against being able to manually release the engaging member. The engaging member can engage with the guiding track or groove during only a part of the shifting movements of the needle protecting sleeve. In some preferred embodiments, the engaging member engages with the guiding track or groove during all of the shifting movements of the needle protecting sleeve.

In some optional embodiments, the engaging member can be in engagement with an abutment which acts in the distal direction, for example an abutment of the housing, when the needle protecting sleeve is in its initial position. The engagement is such or the engaging member and the abutment are formed such that a movement of the needle protecting sleeve out of its initial position toward its extended position can only be released by applying a force which acts in the distal direction to the needle protecting sleeve, in addition to the force generated by the biasing spring. The abutment is not an end abutment which prevents any movement of the needle protecting sleeve in the axial direction but rather a releasable abutment or intermediate abutment which hampers a movement of the needle protecting sleeve in the distal direction. Given a sufficiently large force, the engaging member can snap over the abutment and/or be moved past the abutment. In other words, the engagement can be released by a force which exceeds the force required for shifting movement of the needle protecting sleeve.

In some preferred embodiments, the needle protecting sleeve is arranged on the device such that the needle protecting sleeve can be moved out of its initial position toward its extended position by applying a force which acts in the distal direction, in addition to the force exerted on the needle protecting sleeve by the biased spring. The spring element is configured such that the force exerted by it on the needle protecting sleeve is smaller than the force necessary for a movement of the needle protecting sleeve out of its initial position toward an extended position. This enables the needle protecting sleeve to be prevented from being moved from its initial position to the extended position by the spring force. Only when muscular strength is additionally exerted on the needle protecting sleeve is the force holding the needle protecting sleeve in its initial position overcome, such that the needle protecting sleeve is moved in the distal direction.

The needle protecting device in accordance with the present invention can optionally also serve to remove a needle protecting cap from a needle. The needle protecting sleeve can be coupled or can be able to be coupled to the needle protecting cap such that the needle protecting cap can be removed from the needle by a movement of the needle protecting sleeve. This is advantageous since in certain installed locations, the needle protecting cap is impossible or at least difficult for the user of the device to grip, which hampers removing it. The present invention facilitates removing the needle protecting cap, since the user can remove it from the needle even when it is inaccessible or hardly accessible. In some embodiments, as opposed to technical solutions in which a cap is fastened to the distal end of the device and removed from the distal end before the device is used, thereby slaving the needle protecting cap, the needle protecting sleeve of the present invention remains on the device.

In the optional embodiments, the needle protecting cap can be removed from the needle by a movement of the needle protecting sleeve, relative to the housing, toward an extended position of the needle protecting sleeve. The needle protecting sleeve can be able to be moved from an optional initial position, which the needle protecting sleeve assumes in a delivered or initial state of the device, into the extended position. The initial position can be the retracted position or a position in which the needle protecting sleeve is arranged axially between the retracted position and an extended position of the needle protecting sleeve.

In some preferred embodiments, the needle protecting sleeve can be drawn out of the housing, e.g. from the initial position of the needle protecting sleeve, toward an extended position by the user of the device, by a movement in the distal direction. The needle protecting sleeve can surround the needle protecting cap in its initial state and during the movement into the extended position. The needle protecting cap can be deflected or removed from the needle as the needle protecting sleeve is drawn out. The needle protecting sleeve can slave the needle protecting cap. As the needle protecting sleeve is drawn out of the housing to remove or deflect the needle protecting cap, there is no relative movement or no substantial relative movement between the needle protecting cap and the needle protecting sleeve. The needle protecting cap can be drawn out exclusively or partially using the muscular strength of the user. The user can grip the needle protecting sleeve and draw it out of the housing. To this end, the needle protecting sleeve can comprise a gripping element such as a structured surface or a projection which is directed outward and encircles the needle protecting sleeve annularly. Such a projection can, for example, also serve for an abutment into which it passes, for example with the distal end of the housing, when the needle protecting sleeve is in its retracted position.

In some embodiments, the needle protecting device can also comprise an engaging element which acts on or engages with the needle protecting cap. The needle protecting sleeve and the engaging element are coupled such that the needle protecting cap is slaved in the movement of the needle protecting sleeve to its extended position. The needle protecting cap can thus be deflected from the needle. The engaging element can for example be a separate part which is coupled to the needle protecting sleeve, such as a metal ring which engages laterally with the needle protecting cap by material deformation on the part of the needle protecting cap. In some preferred embodiments, the engaging element is formed in one part with the needle protecting sleeve. The engaging element is arranged at one end of an arm, another end of which is fastened to the needle protecting sleeve. The arm can extend in the longitudinal direction of the needle protecting sleeve or the device, from the proximal end of the needle protecting sleeve in the proximal direction. Here, too, it is advantageous to injection-mold the needle protecting sleeve from plastic. The engaging element can be hook-shaped, such that it acts on or engages with the needle protecting cap. The engaging element engages with the flank of the needle protecting cap or acts on the proximal end of the needle protecting cap, between the needle protecting cap and a drug portion of the product container. The drug portion can be defined as the portion of the product container in which the piston can be shifted and/or in which the drug is accommodated. When the needle protecting sleeve is moved from its initial position to the extended position, the needle protecting cap which is fastened to the needle support or the fastening portion in a positive fit and/or a force fit is deflected from the needle and/or the needle support or the fastening portion via the engagement of the at least one engaging element. The engagement between the at least one engaging element and the needle protecting cap is retained until the needle protecting sleeve is detached from the needle support or the fastening portion.

In some preferred embodiments, at least two of the engaging member, the engaging element and the engaging means, such as for example the engaging member and the engaging means, or all of the engaging member, the engaging element and the engaging means can be formed in one part on the needle protecting sleeve which is produced as an injection-molded part.

In some preferred embodiments, in the first extended position, the engaging member of the needle protecting sleeve is optionally in or can optionally be moved into an engagement with an abutment which acts in the proximal direction, which hampers a movement of the needle protecting sleeve in the proximal direction, wherein the engagement can be released by applying a force which acts on the needle protecting sleeve in the proximal direction. The engaging member can snap over the abutment and/or be moved past the abutment when a sufficiently large force acting in the proximal direction is exerted on the needle protecting sleeve. The sufficiently large force may be, for example, significantly greater than the force which the spring element exerts on the needle protecting sleeve.

In some embodiments, the present invention also presents ways of securely administering liquid drugs in which the active agent(s) is/are in danger of contamination by air, such as formulations which contain FSH or an FSH variant as their essential active agent, or another active agent or drug mentioned here, wherein a concern is to avoid the use of preservatives, not least in view of negative effects on the respective active agent or agents, but also in view of the additional costs which arise by adding preservatives. In accordance with the present invention, the product container—which can also be referred to as a reservoir—comprising the unpreserved liquid drug is dispensed to the patient, e.g. in the form of a complete administering apparatus or a part of the apparatus which can be assembled by simple hand movements. The unpreserved drug which is in danger of contamination in the presence of air is securely stored in the reservoir which is sterilely sealed until immediately before administering, such that the drug can be stored in this state for a period of several days or, for that matter, even months or years. The sterility is maintained until immediately before the drug is used by the patient or an administering physician.

In some embodiments, an administering apparatus which comprises a sequence controller and in which the reservoir is sterilely sealed and contains a liquid drug in the form of for example a liquid formulation of FSH or an FSH variant or other drug mentioned herein may be preferred. The use of carpoules or syringes which contain an unpreserved drug, for example FSH or an unpreserved FSH variant, in a sterile state and therefore non-perishable even without preservatives, is however itself also a subject of the present invention. An administering apparatus which is incapable of dosing, i.e. which has no dosing member, may also be a preferred embodiment, although the option of individual dosing by the patient personally is also highly advantageous for administering such drugs. Other drugs which can be stored in accordance with the present invention in an unpreserved state in a sterilely sealed reservoir of the administering apparatus and can thus be stored for a practically unlimited period of time in commercial circulation, with the physician or also even with the respective patient, are for example neuroleptic drugs (fluphenazine decanoate), vasodilative agents (epinephrine), blood products (etamsylate, epoetin alfa, filgrastim (G-CSF), nadroparin calcium, desmopressin acetate), drugs for treating rheumatic diseases (methotrexate, etanercept), oncological drugs (cladribine, human interferon gamma-1b ADN) and drugs for treating infectious diseases (herpes simplex type 1type 2, human immunoglobin). Usual or preferred active agents for each group of drugs are given in brackets.

In some embodiments, an FSH-based drug contains an alpha subunit and a beta subunit. The proteins for the formulations which can be used can be obtained by various methods. The FSH which is to be used is a heterodimer comprising an α subunit and a β subunit, as described in more detail in EP 1 188 444 A1. In some preferred embodiments, a formulation of FSH and/or an FSH variant in an aqueous solvent is administered using the device in accordance with the present invention. The expression "aqueous solvent" refers to a liquid solvent which contains water. Aqueous solvent systems can consist of water only or can consist of water and one or more miscible solvents and can contain other dissolved constituents (solutes) such as for example sugar or other inactive ingredients. The miscible solvents which are conventionally used are the short-chain organic alcohols such as methanol, ethanol, propanol, short-chain ketones such as acetone, and polyalcohols such as glycerine. For injection purposes, the solvent system consists of water only. Inactive ingredients can be selected from isotonicity agents, preservatives, buffer systems, phosphate buffers, thioether compounds such as methionine as antioxidants, dispersants and/or emulsifiers such as poloxamers and mixtures of them. The formulation does not contain any preservatives, e.g. any preservative of the group consisting of phenol, m-cresol, chlorocresol, a paraben selected from methylparaben, ethylparaben, propylparaben or butylparaben, benzalkonium chloride, benzethonium chloride, sodium dehydroacetate, benzyl alcohol and thiomersal. It may also be preferred if the formulation is free of polycarboxylic acids, oligocarboxylic acids and dicarboxylic acids and of glycine and/or glycerine.

For administering unpreserved liquid drugs, such as administering liquid formulations of FSH or an FSH variant, it may be advantageous if only a drug quantity which is at most as large as a daily dosage is stored in the sterilely sealed reservoir or at most as large as a maximum dosage (single dosage) in which the drug in question is administered in a single administration of a few minutes' duration at most, e.g. a single injection. The reservoir and therefore also the administering apparatus are therefore a reservoir and an administering apparatus for a single dosage of the drug. The maximum dosage for drugs based on for example FSH or an FSH variant is typically 300 IU, in exceptional cases 500 IU, as measured over a multitude of patients. In the case of such a drug, the drug quantity situated in the reservoir therefore corresponds to a dosage of 500 IU at most, or 300 IU at most, in some preferred embodiments. Since a majority of patients only require significantly lower dosages for each individual administration, for example 200 IU at most or even only 100 IU at most, the content amount in such a therapy can advantageously also correspond at most to this dosage.

In further embodiments of the present invention, the administering apparatus supplied each comprise a reservoir which comprises a content amount which is precisely adapted to the actual requirement of the respective patient. Administering apparatus which are identical in design can then, for example, be used in two, three or more different content-amount variants. In the case of an FSH-based therapy, for example, administering apparatus can be supplied which are identical in design and differ from each other substantially only with regard to the content amount of their reservoir, one apparatus for example comprising a reservoir which contains 300 IU of the drug, another apparatus containing 200 IU of the same drug, and another apparatus containing 100 IU of the drug, each in a sterile state. Another sub-division into intermediate increments is also possible, for example in the form of a fourth content-amount variant comprising a reservoir which contains 150 IU of the drug in a sterile state. In general terms, the dosages for FSH can range between 75 IU up to 300 IU, in exceptional cases up to 500 IU. The apparatus is designed for single use as a disposable item in each case and can advantageously be disposed of with the household waste. Not until immediately before administering is the drug in the reservoir—which is sterilely sealed up until this point in time—used in contact with the outside environment.

Various embodiments can be considered for the sterile seal on the reservoir. In one variant, the reservoir is formed by a carpoule which comprises an outlet for administering which is sterilely sealed by a septum which can be pierced. In such embodiments, the drug is sterilely enclosed between the septum and a piston which can be axially moved. Such a reservoir is used together with a needle unit comprising a needle holder and an injection needle which protrudes through the needle holder. The needle holder serves to hold the injection needle and to establish the fluid connection between the needle and the reservoir. For the connection, the reservoir itself or the housing can comprise a connecting portion in the region of the outlet of the reservoir. The connecting portion and a connecting portion of the needle holder are designed to co-operate, such that when the mechanical connection between the needle holder and the connecting portion of the reservoir or housing is established, the injection needle pierces the septum. Once the septum has been pierced, the interior space of the reservoir is connected to the environment via the needle. Once this fluid connection has been established, the drug is administered with as little delay as possible. The administering apparatus or at least a part of the apparatus which contains the completely or partially emptied reservoir, or as applicable the reservoir only, is then disposed of. In a second variant, a syringe or syringe-like structure forms the reservoir. Unlike the first variant, the reservoir of the second variant already comprises an injection needle at its distal end, such that the fluid connection between the reservoir and a downstream outlet of the injection needle inherently already exists. The sterile seal is ensured by an external sealing element, such as a needle protecting cap described herein, which sterilely seals the needle outlet. The sealing element is removed immediately before use.

In one embodiment, in which the drug is already contained in the reservoir in exactly the dosage which is to be delivered by a single administration, it is possible to omit the feature of the ability to dose the drug; correspondingly, the dosing member can be omitted. It is also advantageous in such embodiments if the administering apparatus features a priming function. The priming function can be fulfilled by the conveying member, by blocking it in a releasable blocking engagement in the initial state of the administering apparatus, wherein it has to be moved out of said engagement by applying a force or torque. The short priming stroke expels a volume from the reservoir which is predetermined by the length of the priming stroke. The end of the priming stroke may be defined by a priming abutment. In contact with the priming abutment, the conveying member can then perform the delivery movement. The delivery movement is an axial movement in an advancing direction. The priming stroke is likewise an axial movement in the advancing direction. Between the priming stroke and the delivery stroke, a transverse movement of the conveying member is advantageously required and also only possible once the priming stroke has been performed, thus securely separating priming and delivery from each other.

Even in therapies using an unpreserved drug or a reservoir filled for a single administration only, i.e. a single dosage, it may be advantageous if the administering apparatus features the ability to dose the drug, i.e. comprises the aforementioned dosing member. In this way, despite an optional variety of variants with regard to the content amount for a respective single administration only, it is possible to set the dosage even more precisely in each variant. In other words, by providing a plurality of content-amount variants, it is possible to reduce the drug quantity as a whole, as considered over a large number of patients, i.e. as compared to embodiments in which the reservoir respectively contains the maximum dosage which is ever delivered in a single administration within the therapy. Conversely, the individual patient can even more individually set the dosage tailored to them, within the suitably selected content-amount variant, and administer only this dosage.

DETAILED DESCRIPTION

The embodiment of an administering apparatus in accordance with the present invention shown in the accompanying figures is an elongated injection pen. The administering apparatus is designed for single use, for a single injection of a liquid drug which can be a liquid formulation based on FSH or an FSH variant for a hormone treatment for stimulating the ovaries and consequently, by fertilising the stimulated egg cells, pregnancy. The liquid drug, i.e. the liquid formulation, is unpreserved, i.e. does not contain any preservatives. If, as may be preferred, the drug is a formulation which contains FSH or an FSH variant, it therefore has to be administered within a few minutes, at any rate within a few hours, after contact with the ambient air.

Figure 1:
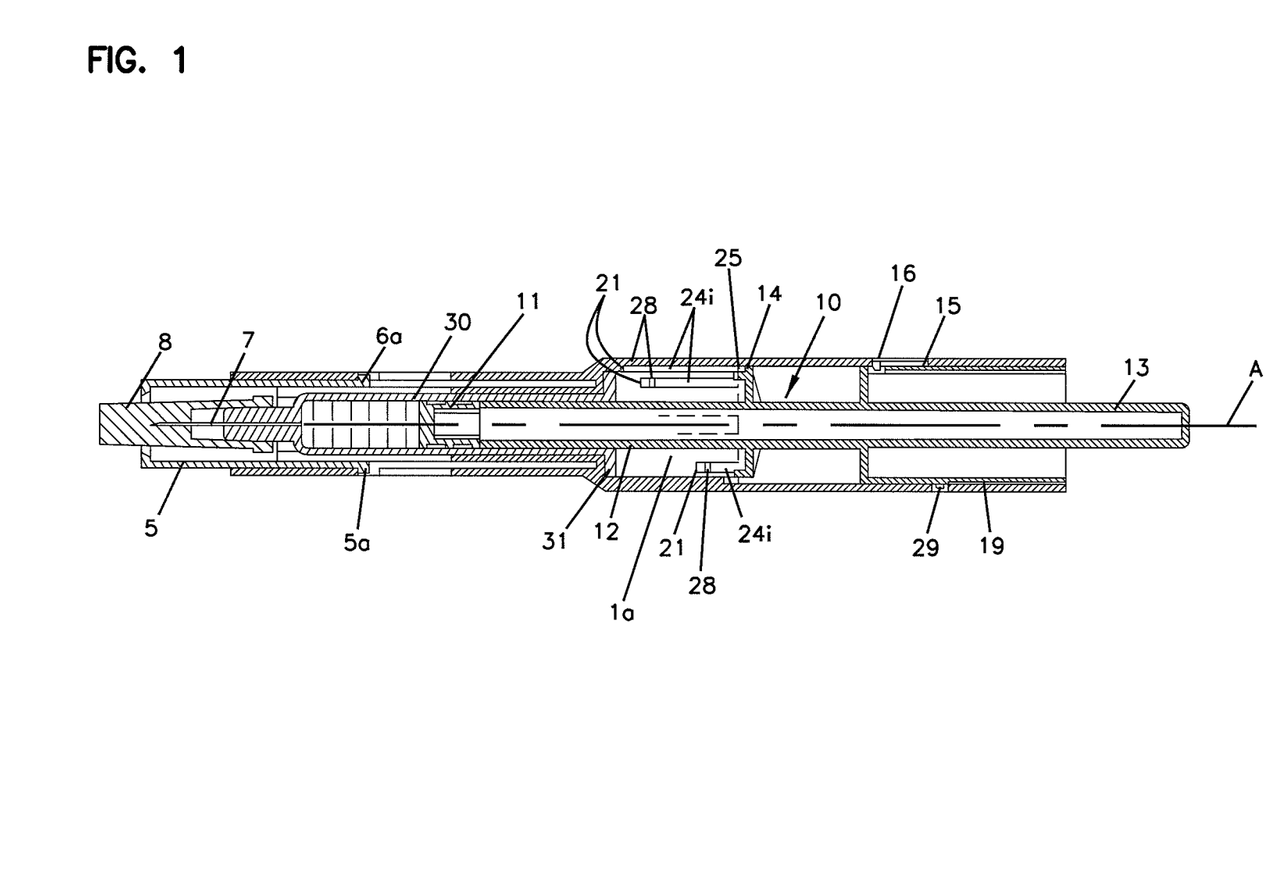
FIG. 1 depicts an embodiment of an administering apparatus in accordance with the present invention in an initial or delivered state, with a needle protecting cap placed on it.
Figure 8A:
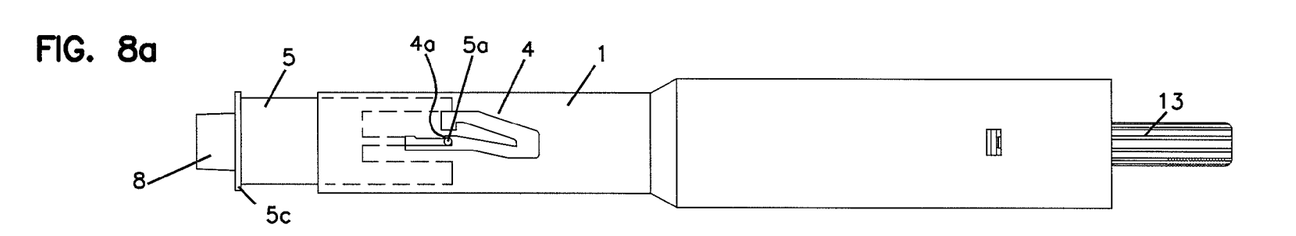
FIGS. 8a-8d depict an alternative guiding track for the administering apparatus of FIG. 1.

FIGS. 1 and 8a show administering apparatus in an initial or delivered state before use, wherein the administering apparatus from FIG. 8a is equipped with an alternative guiding track 4. The patient is provided with the apparatus in this state. The apparatus comprises a sleeve-shaped housing 1 comprising a front, distal housing portion in which a reservoir 30 is accommodated which contains the drug in a sterile state, and a rear, proximal housing portion in which structures are formed which co-operate with a dosing and conveying means of the apparatus, to enable the patient to individually select a dosage of the drug to be administered. The proximal housing portion can also serve as a gripping part of the apparatus. An operating element 13 of the dosing and conveying means, which protrudes out of the housing 1 in the proximal direction at the proximal end, can be seen.

A dosage display window 2 and a reservoir window 3 are formed in the housing 1. The dosage set can be read through the window 2, and the reservoir 30 can be seen through the window 3. The distal end of the reservoir 30 comprises a connecting portion to which a needle 7 is non-releasably fastened. A needle protecting cap 8 fastened to the reservoir 30 is not detached from the needle 7 until immediately before administering, to ensure the sterility of the drug up until this point in time.

As mentioned, FIGS. 1 and 8a show the administering apparatus in its initial state with the reservoir 30 sterilely sealed, more specifically in its storage state in which the apparatus can be stored for a longer period of at least several months, since the airtight, sterile seal on the reservoir 30 ensures the non-perishability of drugs, including unpreserved drugs. To administer the drug, the patient removes the needle protecting cap 8 from the needle 7 immediately before administering. In the example of FIG. 1, the patient grips the needle protecting cap 8 and removes it from the needle 7. In the example of FIGS. 8a-8d, the patient removes the needle protecting cap 8 with the aid of a needle protecting sleeve 5.

Figure 7:
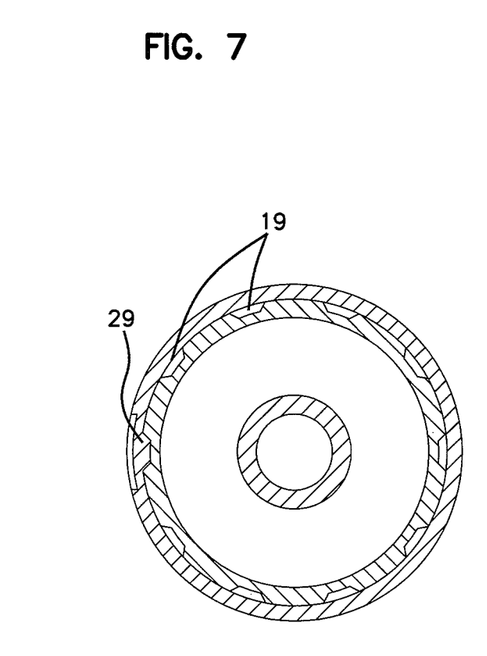
FIG. 7 shows the region of a dosing locking element of the administering device of FIG. 1.
Figure 8B:
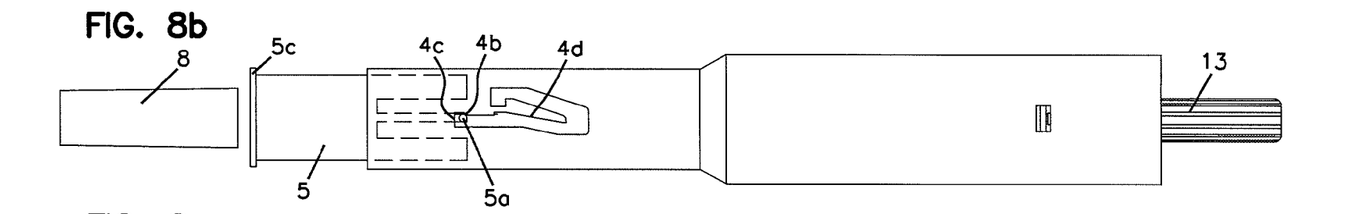
Figure 8C:
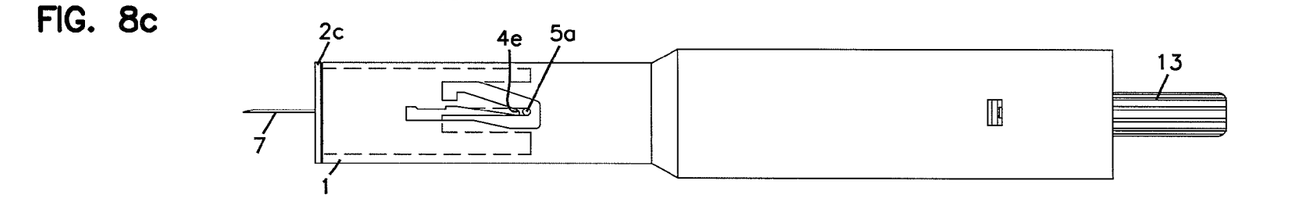

Referring to FIGS. 8a and 8b, a means is described with the aid of which the needle protecting cap 8 can be removed from the needle 7. This means can be used as additional equipment for the device of FIGS. 1 to 7. In the initial position of the needle protecting sleeve 5 shown in FIG. 8a, which the needle protecting sleeve 5 assumes in relation to the housing 1 in the delivered state of the optional injection device, the needle protecting sleeve 5—for example, at least one engaging element of the needle protecting sleeve 5—acts on or engages with the needle protecting cap 8, for example between a drug portion of the product container and the proximal end of the needle protecting cap 8, or engages laterally with the needle protecting cap 8.

The needle protecting sleeve 5 comprises an arm which extends from the proximal end of the needle protecting sleeve 5 in the proximal direction and has a proximal end at which an engaging member 5a is formed which engages with a guiding track 4 formed by the housing 1. By being arranged on the arm, the engaging member 5a is spring-elastic transverse to the longitudinal axis of the device, while it is substantially fixed relative to the needle protecting sleeve 5 along the longitudinal axis. The engaging member 5a is cam-shaped and points radially outward into the guiding track 4 which is open toward the inner side of the housing 1.

An abutment 4a which acts in the distal direction is formed on the flank of the groove-shaped guiding track 4, for engaging with the engaging member 5a. The engagement is configured such that it cannot be released by the force of the biased spring element 6 only.

By applying an additional force, e.g. the muscular strength of the user, to the needle protecting sleeve 5 in the distal direction, the engagement with the abutment 4a is released by the engaging member 5a snapping over the abutment 4a. This moves the needle protecting sleeve 5 in the distal direction, from its initial position into its first extended position and past the abutment 4a. To, among other things, improve the user's ability to grip the needle protecting sleeve 5, the needle protecting sleeve 5 comprises a projection 5c which annularly points radially outward.

At the end of the movement of the needle protecting sleeve 5 to its first extended position, the engaging member 5a abuts against an end abutment 4c which acts in the distal direction but blocks the needle protecting sleeve in the distal direction, even when an increased force is applied.

As it moves in the distal direction, the needle protecting sleeve 5 slaves the needle protecting cap 8 via the at least one engaging element, such that the needle protecting cap 8 is detached or deflected from the product container and/or the fastening portion. The needle protecting cap 8 can thus be removed from the device (FIG. 8b).

When the needle protecting sleeve 5 is in its first extended position, as shown in FIG. 8b, a movement of the needle protecting sleeve 5 in the proximal direction, i.e. into a retracted position, is hampered by an engagement between the engaging member 5a and the abutment 4b. Applying a force which acts in the proximal direction and is, for example, significantly greater than the force which would be required if the needle protecting sleeve 5 only had to be pushed counter to the spring force of the spring element 6, snaps the engaging member 5a over the abutment 4b, thus shifting the needle protecting sleeve 5—the distal end of which is, pressed onto the injection point—abruptly into the housing 1 until the projection 5c abuts against the distal end of the housing 1. Abruptly pushing back the needle protecting sleeve 5, which is achieved by the engagement between the engaging member 5a and the abutment 4b, injects the needle 7 into the patient. The remaining movement sequence of the engaging member 5a in the guiding track 4 from FIGS. 8a-8d corresponds to the movement sequence of the engaging member 5a in the device from FIGS. 1-7.

Once the needle protecting cap 8 has been removed, the drug is connected to the environment and has to be administered within a short period of time, optimally without delay, if the drug is an unpreserved drug based on FSH or an FSH variant, as may be preferred.

The device from FIGS. 1-7 likewise comprises a needle protecting sleeve 5 which is mounted or carried by the housing 1. In FIGS. 1, 2a and 2b, the needle protecting sleeve is situated in its initial position, i.e. in a first extended position. In its extended position, the needle protecting sleeve 5 extends distally beyond the distal end of the needle tip.

As can best be seen from FIGS. 2a-4a, the needle protecting sleeve 5 comprises an arm which extends from the proximal end of the needle protecting sleeve 5 in the proximal direction and has a proximal end at which an engaging member 5a is formed which engages with a guiding track 4 formed by the housing 1. By being arranged on the arm, the engaging member 5a is spring-elastic transverse to the longitudinal axis of the device, while it is substantially fixed relative to the needle protecting sleeve 5 along the longitudinal axis. The engaging member 5a is cam-shaped and points radially outward into the guiding track which is open toward the inner side of the housing 1. The engaging member 5a, including the arm carrying engaging member 5a, is formed in one part on the needle protecting sleeve 5.

When the needle protecting sleeve 5 is in its initial position, the engaging member 5a is in engagement with an end abutment 4c which acts in the distal direction and blocks a movement of the needle protecting sleeve 5 in the distal direction, even when an increased force is applied. It should be noted that this abutment 4c could probably be destroyed by a very large force, wherein such a force is not exerted on the needle protecting sleeve 5 during normal use.

Figure 2A:
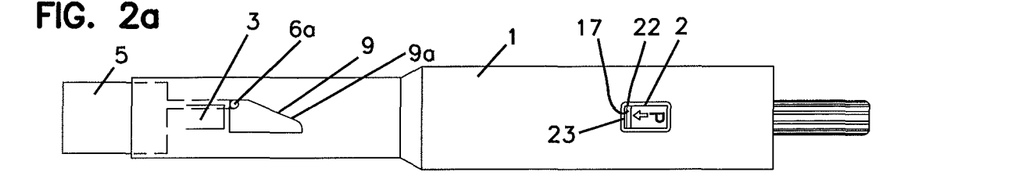
FIGS. 2a and 2b depict the administering apparatus of FIG. 1, with the needle protecting cap removed before priming and with an embodiment of a needle protecting sleeve in accordance with the present invention in its initial position.
Figure 2B:
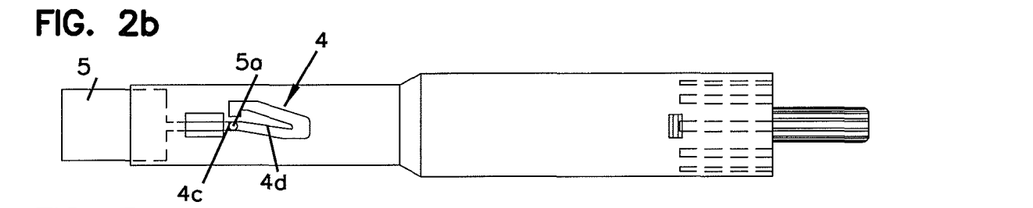
Figure 3A:
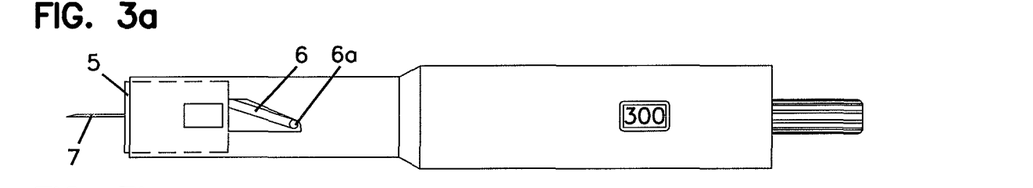
FIGS. 3a and 3b depict the administering apparatus of FIG. 1 after it has been primed and a dosage has been set and with the needle protecting sleeve in a retracted position.
Figure 3B:
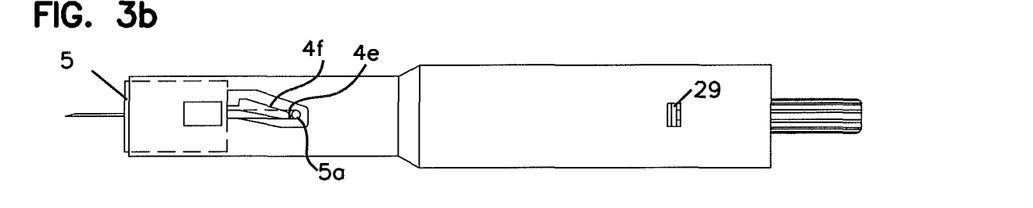

When the needle protecting sleeve 5 is in its first extended position, i.e. its initial position as shown in FIGS. 2a and 2b, a movement of the needle protecting sleeve 5 in the proximal direction is possible. By applying a force which acts in the proximal direction, for example by pressing the distal end of the needle protecting sleeve 5 onto an injection point, the needle protecting sleeve 5 is shifted into the housing 1, counter to the force of a spring element 6 as explained further below. Once the needle protecting sleeve 5 has been pushed back into the housing 1 and/or the retracted position (FIGS. 3a and 3b), the needle 7 protrudes beyond the distal end of the needle protecting sleeve 5 in accordance with the desired injection depth e.g. for a subcutaneous injection.

An arm which serves as a spring element 6 protrudes from the proximal end of the needle protecting sleeve 5 in the proximal direction. The arm 6 comprises an engaging means 6a which protrudes outward in the shape of a cam into a link, e.g. a spring link 9. The engaging means 6a is substantially axially fixed with respect to the needle protecting sleeve 5 and can be moved springing transverse to the longitudinal axis of the needle protecting sleeve 5. The spring element 6 including the engaging means 6a is formed in one part with the needle protecting sleeve 5. When the needle protecting sleeve 5 is pushed back into the housing 1, the engaging means 6a slides off on a guiding area 9a which is inclined transverse to the longitudinal axis of the device, thus deflecting the spring element 6 and the engaging means 6a transverse to the longitudinal axis of the needle protecting sleeve 5. This tenses the arm 6 with a bending moment or elastically deforms it. The force exerted on the guiding area 9a by the engaging means 6a and/or the reaction force exerted on the engaging means 6a by the guiding area 9a generates a force component which acts in the distal direction and is channelled onto the needle protecting sleeve 5 via the arm 6. As it is pushed back into the housing 1, the needle protecting sleeve 5 is moved counter to this force and/or force component of the spring force component of the spring 6 is dependent on the inclination of the guiding area 6a in relation to the longitudinal axis.

The guiding track 4 comprises a flank 4d which, when the needle protecting sleeve 5 is pushed back from its first extended position (FIGS. 2a, 2b and 8b) into its retracted position (FIGS. 3a, 3b and 8c), deflects the engaging member 5a transverse to the longitudinal axis of the device and spring-elastically biases the arm on which the engaging member 5a is arranged. When or before the needle protecting sleeve 5 has reached its retracted position, the engaging member 5a snaps back out of its deflected position. The arm on which the engaging member 5a springs back once the needle protecting sleeve 5 has been retracted is in a relaxed position. The sprung-back engaging to member 5a is axially flush with a switching portion 4e of the guiding track 4 which prevents the engaging member 5a from being deflected back in the direction from which it has snapped during the retracting movement of the needle protecting sleeve 5. The switching portion 4e is also formed, e.g. with an oblique area, such that when the needle protecting sleeve 5 is moved out of the retracted position in the distal direction, to a second extended position, the engaging member 5a is deflected in the same direction as it springs back when retracted, after it has passed the guiding area 4d of the needle protecting sleeve 5. When the needle protecting sleeve 5 moves from the retracted position into the second extended position, which occurs when the needle 7 is drawn out of the patient, wherein the biased spring 6 keeps the needle protecting sleeve 5 pressed on the injection point, the engaging member 5a is deflected transverse to the longitudinal direction of the injection device by the switching element 4e and another guiding area 4f, thus biasing the arm which acts as a spring and connects the engaging member 5a and the needle protecting sleeve 5.

Figure 4A:
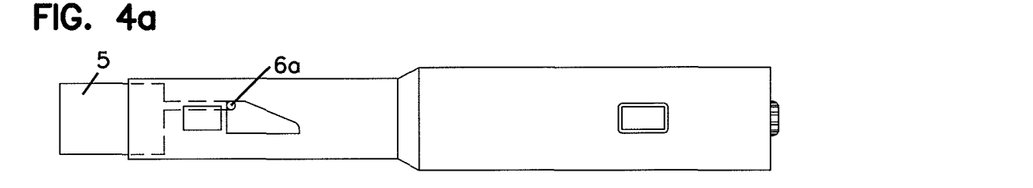
FIGS. 4a and 4b depict the administering apparatus after a dosage has been delivered and with the needle protecting sleeve in an end position.
Figure 4B:
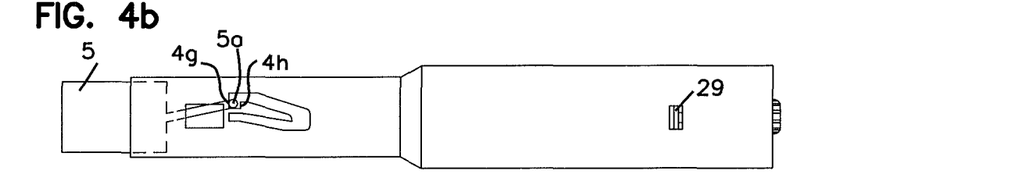
Figure 8D:
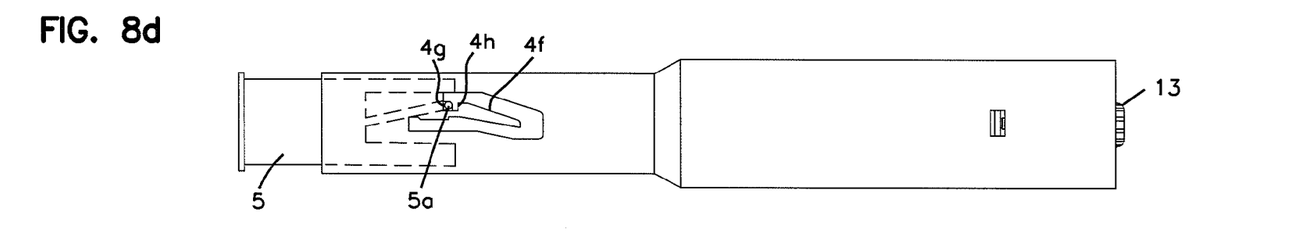

At the end of the movement of the needle protecting sleeve 5 to its second extended position, the engaging member 5a springs back transverse to the longitudinal axis of the device, i.e. in the direction from which it was deflected as the needle protecting sleeve 5 moved from its retracted position to its second extended position. The needle protecting sleeve 5 is prevented from moving in the distal direction by an end abutment 4g which acts in the distal direction. The needle protecting sleeve 5 is prevented from moving in the proximal direction by an abutment 4h which acts in the proximal direction. In the second extended position, the engaging member 5a is situated between the abutments 4g and 4h, such that the needle protecting sleeve 5 can be latched axially fixed, aside from a small clearance, to the housing 1 (FIGS. 4a, 4b and 8d).

An advantage of the device is that the needle protecting sleeve 5, including the arm on which the engaging member 5a is formed and the arm 6 which acts as a spring and on which the engaging means 6a is formed, is manufactured in one part, e.g. injection-molded from a plastic. This enables the price of manufacturing the needle protecting sleeve 5 and of its final assembly to be lowered.

The device is disposed of once it has been used, wherein the danger of injury from the needle 7 is reduced by the latched needle protecting sleeve 5.

Although the administering apparatus is designed for single use only, i.e. a single injection only, and is disposed of after use with the household waste as a disposable item, it nonetheless comprises a whole range of features which are usually only found in administering apparatus which are used repeatedly. On the one hand, the administering apparatus features the ability to select the dosage, such that the patient can personally set the dosage which they wish to administer. The reservoir 30 which is filled by the manufacturer contains a maximum dosage of the drug which is set such that, as considered over a larger group of potential patients, it is sufficient for each of said patients. Persons who only require a lower dosage for each administration can set this lower dosage themselves. Once used, the apparatus is disposed of together with the residual amount of the drug which correspondingly still remains in the reservoir 30. The apparatus also features the ability of priming, i.e. of venting the reservoir 30. Priming the apparatus may be forced by a design feature, i.e. the patient must first prime the apparatus before a dosage can be set and administered. Priming displaces any free gas which may be contained in the reservoir 30, e.g. nitrogen or air, out of the reservoir 30. Air can enter the reservoir 30 during manufacture, when the reservoir 30 is being filled. On the one hand, this air or other gas as applicable should not be administered; on the other hand, however, it also distorts the dosage, since the administered dosage would deviate from the dosage set by the amount of gas which, without priming, is situated in the reservoir 30.

The administering apparatus comprises a conveying means 10 comprising a first conveying member 11 and a second conveying member 12. The first conveying member 11 is a piston 11 accommodated such that it can be moved within the reservoir 5 and which sterilely seals the reservoir 5 at one end and can be moved within the reservoir 30 in an advancing direction along a central longitudinal axis A of the apparatus toward the outlet. The injection needle 7 likewise extends axially on the axis A. The second conveying member 12 forms a piston rod. The conveying member 12 is only in an axial pressing contact with the piston 11, i.e. when the apparatus is activated, the conveying member 12 presses the piston 11 in a loose pressing contact axially toward the outlet of the reservoir 5. Alternatively, the conveying member 12 can be connected axially fixed, both counter to and in the direction of the outlet of the reservoir 5, to the piston 11.

The conveying member 12 also forms a dosing means together with the housing 1. The conveying member 12 is therefore referred to in the following as the dosing and conveying member 12. To fulfil the dosing function, the dosing and conveying member 12 can be rotationally moved relative to the housing 1 about the axis A, i.e. when the dosage is being set, the dosing and conveying member 12 performs a rotational dosing movement about the axis A. To fulfil the conveying function, the dosing and conveying member 12 can be translationally moved along the axis A in the advancing direction. A proximal end portion of the dosing and conveying member 12 also forms the activating element 13. The patient sets the dosage on the activating element 13 and also initiates the delivery movement of the dosing and conveying member 12 by exerting a pressure force in the advancing direction. To fulfil the different functions, i.e. priming, dosing and conveying and/or delivery, the dosing and conveying member 12 comprises a plurality of structural elements, e.g. a first dosing element 14 for dosing which simultaneously also forms a delivery abutment and thus itself fulfils both a dosing function and a delivery function. A dosing blocking element 16 is another of these structural elements.

When the dosage is being set, the first dosing element 14 co-operates with a plurality of second dosing elements $24_i$ which are arranged in a distribution about the longitudinal axis A and formed in a dosing portion 1a of the housing 1 on its inner surface area. The dosing elements $24_i$, where i=1, 2, 3. . . n, are axial guides for the first dosing element 14 which co-operates as an engaging element with said guides $24_i$. The dosing elements and/or guides $24_i$ exhibit different axial lengths, wherein these lengths each correspond to a dosage which can be set. The dosing elements $24_i$ are for example formed as axial blind grooves on the inner circumference of the dosing portion 1a. The blind grooves are open at their proximal ends, such that the first dosing element 14 can move in the advancing direction into one of these grooves $24_i$ in accordance with the rotational angular position of the dosing and conveying member 12 and can be moved in the advancing direction in the course of a delivery stroke in the groove $24_i$ in question, up to its distal end. As already mentioned, the dosing element 14 forms a delivery abutment in a dual function by moving into axial abutting contact against a delivery abutment 21 of the housing 1, formed in the example by the distal end of the respective blind groove $24_i$, at the end of the delivery stroke of the dosing and conveying member 12. The length of the delivery stroke thus corresponds to the length of the dosing element $24_i$ which co-operates with the dosing element 14 in accordance with the dosage set. For dosing, it is alternatively possible to provide a stepped member which is formed in the region of the dosing portion 1a of the housing 1 on its inner surface area. The stepped member comprises a plurality of axial abutments arranged on different axial positions. For dosing, the first dosing element 14 is moved so as to be axially flush with one of the desired axial abutments, in accordance with the rotational angular position of the dosing and conveying member 12. The dosage to be administered, the distance between the first dosing element 14 and the axial abutment selected by the rotational angular position and the dosage to be delivered are related in the same way as the first dosing element 14 and the distal end of the blind grooves $24_i$. As in the previously described alternative, the dosage is administered by moving the first dosing element 14 up to and against the previously selected axial abutment. The stepped member is cost-effective since it does not require any axial blind grooves.

The dosing and conveying member 12 forms a dosing locking means with the housing 1. A dosing locking structure 19 which extends around the rotational axis A is formed on an outer circumference of the dosing and conveying member 12 for this purpose, as can best be seen from FIG. 7. When the dosing and conveying member 12 is rotationally moved, an elastically flexible dosing locking element 29 in the form of a radially flexible snapper which is formed on the housing 1 slides over the dosing locking structure 19. The dosing locking structure 19 is formed in the manner of outer teeth or an outer toothing which is, for example, formed directly on the outer surface area of the dosing and conveying member 12, circumferentially about the axis A, and corresponds in its separation to the separation of the second dosing elements $24_i$, such that the dosing locking element 29 respectively engages with a recess of the dosing locking structure 19 when the dosing element 14 is exactly axially flush with one of the dosing elements $24_i$. In a reversal of this arrangement, a dosing locking structure could also be formed on the inner surface area of the housing 1 and an elastically flexible dosing locking element could be formed on the dosing and conveying member 12.

Figure 9:
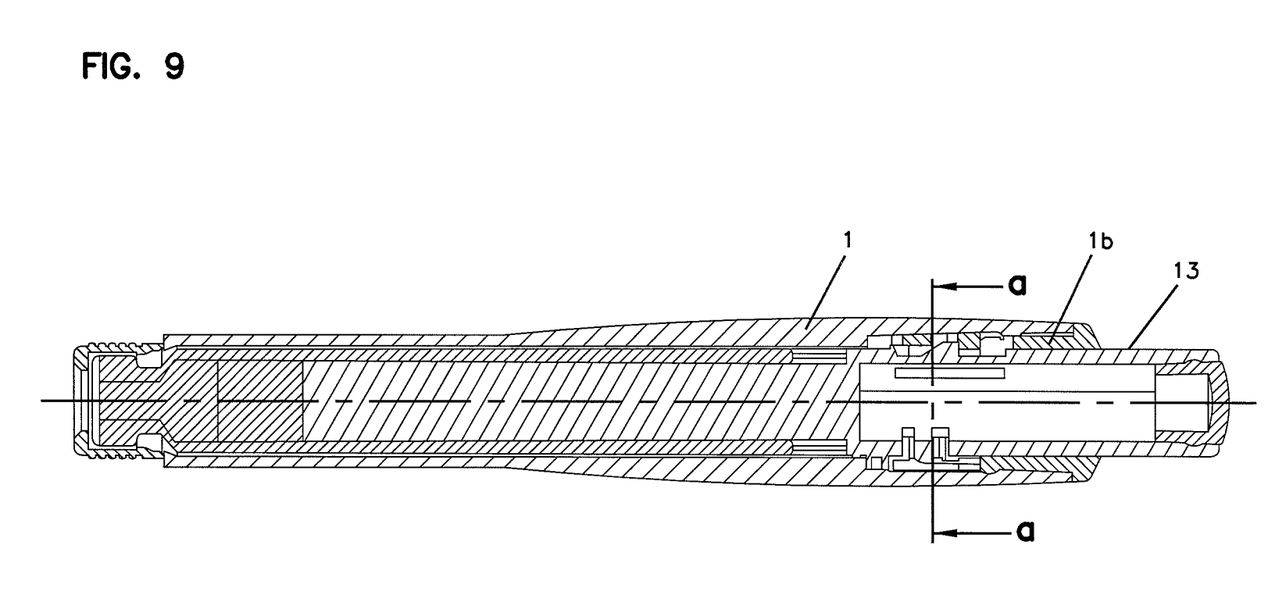
FIG. 9 depicts an administering apparatus in accordance with the present invention modified by an additional sleeve at the proximal (rear) end of the housing.

FIG. 9 shows a modified administering apparatus which, except for the differences mentioned in the following, is designed and/or can be equipped with the needle protecting sleeves described here, as described in FIGS. 1-8. The administering apparatus of FIG. 9 comprises a functional sleeve 1b accommodated at the proximal end of the housing 1 and connected, rotationally and axially fixed, to the housing, in a positive fit, for example snapped onto it. The functional sleeve 1b comprises a portion which is surrounded by the housing 1. The functional sleeve 1b also comprises a portion which forms the proximal end of the housing. This portion comprises a collar which abuts the proximal end of the housing 1 and also terminates flush with the housing 1 in the radial direction. The functional sleeve 1b offers advantages when assembling the administering apparatus. The functional sleeve 1b can comprise the means shown in the rear region of the injection apparatus from FIG. 1. The functional sleeve 1b can perform some or most of the functions of the housing 1 from FIG. 1, e.g. those of rotationally securing before priming and/or ratcheting when setting the dosing and/or axially guiding the piston rod.

To this end, the functional sleeve 1b can comprise the dosing locking element 29 shown in FIG. 7. The functional sleeve 1b can alternatively or additionally form the dosage display window 2 shown in FIG. 6, which forms the rotational abutments 22 and with which the dosing blocking element 16 engages. The functional sleeve 1b can alternatively or additionally comprise the dosing portion 1a shown in FIG. 5 or the dosing elements $24_i$ which are likewise shown in FIG. 5, to longitudinally guide the dosing and conveying member 12.

In the depicted exemplary embodiment, all the functional structural elements are formed either on the housing 1 or on the dosing and conveying member 12. In one equally preferred modification, the dosing blocking element 16 and the dosing locking structure 19 can also be formed separately from the rest of the dosing and conveying member 12, e.g. on a sleeve part corresponding to the sleeve part of the exemplary embodiment, which forms the outer circumference as mentioned in the paragraph above. Such a separately formed sleeve part comprising the dosing blocking element 16 and the dosing locking structure 19 would however be fixedly joined, such that it cannot be moved, to the part of the dosing and conveying member 12 which protrudes through the housing 1 and forms the piston rod. As a result, a joined dosing and conveying member 12 would be obtained which in terms of its shape would correspond to that of the exemplary embodiment.

In the initial state of the administering apparatus (FIGS. 1, 2a and 2b), the dosing and conveying member 12 is situated in a dosing blocking engagement in which it is prevented from being rotationally moved about the axis A. The dosing blocking engagement is effected by the dosing blocking element 16 which is likewise formed on the dosing and conveying member 12, as can be seen in FIG. 6. The dosing blocking element 16 is in the dosing blocking engagement with the housing 1. For this purpose, the housing 1 forms a rotational abutment 22 as a blocking counter element. The dosing blocking engagement is formed in that the dosing blocking element 16 protrudes into the dosage display window 2 in the initial state in which the dosing and conveying member 12 assumes its rearmost position, in relation to the advancing direction, relative to the housing 1 and the reservoir 30, such that the left-hand and right-hand side wall of the dosage display window 2 each act as a rotational abutment 22 clockwise and anti-clockwise about the axis A.

FIG. 6 shows an enlarged detail of the region in which the dosing blocking engagement exists in the initial state of the apparatus. The dosing blocking element 16 protrudes radially outward over an outer circumferential area of the dosing and conveying member 12, into the dosage display window 2. It is arranged on the dosing and conveying member 12 such that it protrudes into the window 2, immediately behind a front facing wall 23 of the window 2 in relation to the advancing direction, and thus lies axially opposite said facing wall 23 (FIG. 2a). For the dosing blocking engagement, which in the depicted exemplary embodiment is formed as a rotational blocking engagement due to the rotational dosing mobility of the dosing and conveying member 12, the dosing blocking element 16 exhibits a width in the circumferential direction about the axis A—the rotational axis of the dosing and conveying member 12—such that the dosing blocking element 16 almost completely fills the window 2 in the circumferential direction, as can be seen in FIG. 1, i.e. it does not have any "breathing space" in the circumferential direction in the dosing blocking engagement and lies opposite the rotational abutments 22 formed by the two side walls of the window 2 in a virtually tight fit in both rotational directions. The abutment areas of the dosing blocking element 16 which act in the two rotational directions of the rotational mobility are provided with the reference sign 17.

In addition to the two rotational abutment areas 17, the dosing blocking element 16 comprises an axial guiding area 18 which is inclined in relation to the axis A and co-operates with the facing area 23 of the dosage display window 2 which lies axially opposite it. If a sufficiently large axial pressure force is exerted on the dosing and conveying member 12, namely by pressing on the operating element 13, the inclined guiding area 18 of the dosing blocking member 16 is pressed axially against the facing area 23. The dosing blocking member 16 is elastically flexible, radially in relation to the axis A, such that it slides off on the facing area 23 due to the inclined guiding area 18, wherein it moves radially inward and thus out of the dosing blocking engagement with the rotational abutment 22 to the left and right in relation to the rotational direction. The facing area forms an unblocking abutment 23.

When the dosing blocking element 16 has just passed the unblocking abutment 23 in the advancing direction, the dosing and conveying member 12 is free of the dosing blocking engagement and can be rotationally moved about the axis A.

Figure 5:
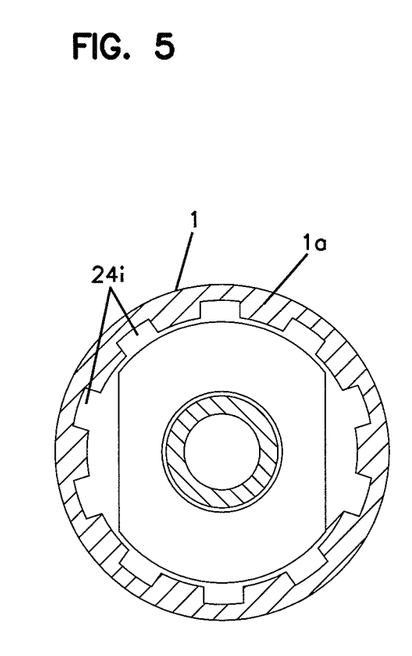
FIG. 5 shows a dosing portion of the administering apparatus of FIG. 1, in cross-section.
Figure 6:
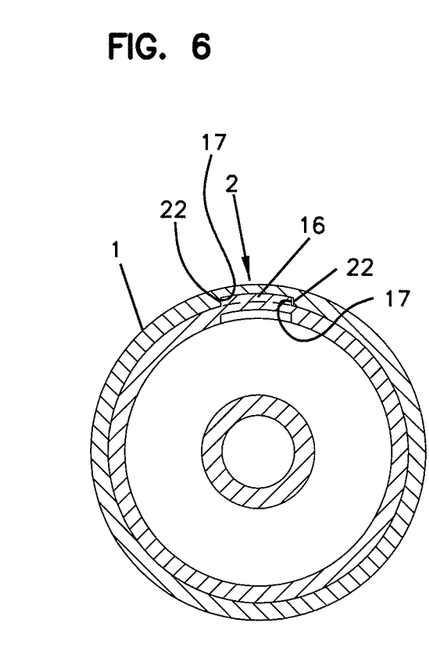
FIG. 6 show the region of a dosing display window of the administering device of FIG. 1, in cross-section.

FIG. 5 shows the administering apparatus in a cross-section in the region of the dosing portion 1a, during delivery of the drug. The dosing element 14 is axially guided by one of the dosing elements $24_i$ formed uniformly around the axis A in the dosing portion 1a, such that during its delivery stroke, the dosing and conveying member 12 necessarily maintains the rotational angular position set when selecting the dosage. FIGS. 6 and 10 show the administering apparatus after the dosage set has been completely delivered, for example after the maximum dosage has been delivered.

The delivery stroke is terminated by the respective delivery abutment 21 at the front end (in the advancing direction) of each of the dosing elements $24_i$, in that the dosing element 14 abuts against the respective delivery abutment 21 of the housing 1 in the advancing direction. Each of the dosing elements $24_i$ comprises a delivery abutment 21 at its front end in the advancing direction, wherein the delivery abutments 21 are formed at different axial levels corresponding to the different dosages.

The administering apparatus exhibits a retaining means for the dosing and conveying member 12. The retaining means ensures that the dosing and conveying member 12, once it has completely performed the delivery stroke, remains in the delivery position which it then assumes. The retaining means comprises retaining elements 28 which are assigned to the dosing elements $24_i$, i.e. one of the retaining elements 28 for each one of the dosing elements $24_i$, respectively. The retaining element 28 of the axially longest dosing element $24_i$ and the retaining element 28 of the axially shortest dosing element $24_i$ can be seen in FIG. 6. The retaining elements 28 are formed by the housing 1 and are, for example, formed on its inner surface area as retaining cams which protrude radially inward. The delivery abutment 14 or dosing element 14, respectively, is inclined in relation to the axis A on a front side which points in the advancing direction, such that it can slide over the retaining element 28 of the respective dosing element $24_i$ in the advancing direction. The rear side of the delivery abutment 14 or dosing element 14, respectively, points at least substantially orthogonally with respect to the axis A, such that in co-operation with the respective retaining element 28, it holds the dosing and conveying member 12 in the latter's delivery position, either blocking it against moving counter to the advancing direction or at least impeding such a retracting movement. This ensures that the administering apparatus cannot be inadvertently and improperly used for another delivery, if the dosage set was smaller than the drug dosage situated in the reservoir 30 in the initial state.

The functionality of an administering apparatus in accordance with the present invention may be explained as follows. The patient is provided with the apparatus in the initial state of FIG. 1. For administering, the patient removes the needle protecting cap 9 from the reservoir 30 which is embodied as a syringe. The reservoir 30 has to be vented before administering. The administering apparatus forces this priming step, since the dosage to be administered cannot be set until after priming. The volume which is expelled during priming is predetermined, namely by the axial clear distance which the delivery abutment 14 exhibits from the priming abutment 25. Prematurely setting the dosage is prevented by the dosing blocking engagement between the dosing blocking element 16 and the rotational abutment 22 of the housing 1. The dosing blocking engagement between 16 and 21 can also be seen in FIG. 1.

In this initial state, the dosage display indicates to the patient that priming has to be performed and how this is done. The display which can be seen in FIG. 1—a pictogram of a directional arrow pointing in the advancing direction and/or a "P" for "priming"—appears in the dosage display window 2. The patient vents the reservoir 30 by exerting an axial pressure force on the operating element 13. The elastically flexible dosing blocking element 16 yields radially inwardly under the pressure force, in that its guiding area 18 slides over the unblocking abutment 23 of the housing 1, whereby the dosing blocking element 16 is moved radially inward, out of the dosing blocking engagement. The priming stroke is limited by the priming abutment 25, i.e. the priming stroke is terminated as soon as the delivery abutment 14 abuts against the priming abutment 25.

The dosing blocking engagement is released directly after the priming stroke has been performed. In this state, the dosage to be administered can be set by rotating the dosing and conveying member 12 about the axis A into a rotational angular position in which the delivery abutment 14, which acts as a dosing element 14 during dosing, is axially flush with the dosing element $24_i$ which in terms of its axial length corresponds to the dosage to be administered. The dosage set can be read in the dosage display window 2 (FIG. 2).

Once the dosage has been set, the patient presses the distal end of the needle protecting sleeve 5 of the administering apparatus onto the desired injection point, which moves the needle protecting sleeve 5 from its first extended position into the retracted position and injects the injection needle 7 into and under the skin. Once the injection needle 7 has been injected, the patient delivers the dosage set by exerting an axial pressure force on the operating element 13 and so moving the dosing and conveying member 12 in the advancing direction, wherein the dosing and conveying member 12 presses against the piston 11 and pushes it through within the reservoir 30 toward the outlet until the delivery abutment 14 of the dosing and conveying member 12 abuts against the delivery abutment 21 assigned to the selected dosing element $24_i$. The delivery stroke of the dosing and conveying member 12 and of the piston 11, i.e. the conveying means 10, corresponds to the axial length of the selected dosing element $24_i$.

Shortly before the end of the delivery stroke, the delivery abutment (dosing element) 14 passes over the retaining element 28 assigned to the selected dosing element $24_i$. The clicking sound thus generated provides the patient with an audible and also tangible signal that the delivery stroke has been completely performed. The dosing and conveying member 12 is then situated in the retaining engagement which prevents the dosing and conveying member 12 from retracting counter to the advancing direction or at least significantly impedes it. As can be seen in FIG. 4a, the dosage display provides a blank display through the window 2. In a further development, the dosage display 15 can be amended to include a pictogram or colour marking or even text in order to provide the patient with a positive content feedback that the dosage set has been completely delivered. The patient can see the piston 11 through the reservoir window 3. As a result, this also visually signals to the patient that the delivery has been completely performed.

Embodiments, including preferred embodiments, have been presented in this application for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for protecting against needle sticks, comprising a needle protection sleeve for being coupled to an administering device to cover a needle associated with the administering device, wherein the sleeve can be moved against the force of a spring from an initial extended position in which the sleeve extends distally beyond a distal end of the needle to a retracted position and by the force of the spring from the retracted position returned to the extended position, the spring being carried on the needle protection sleeve, wherein the spring and the needle protecting sleeve are formed as a monolithic, unitary part, the spring extending linearly from the needle protection sleeve in a proximal direction.

2. The device according to claim 1, wherein the spring and the needle protection sleeve are a single part, the spring being tensed by deflecting it transverse to a longitudinal axis of the sleeve.

3. A device for protecting against injuries from an injection needle, said device comprising:
   a) a housing;
   b) a needle using which a liquid product can be injected; and
   c) a needle protecting sleeve which has an arm extending therefrom in a generally longitudinal axial direction to engage a guiding area of the housing and which can be moved counter to a force generated by elastic deflection of the arm from its axial direction by the guiding area from an initial extended position in which the sleeve extends distally beyond a distal end of the needle into a retracted position and returned by the force generated by elastic deflection from a retracted position into a second extended position.

4. The device according to claim 3, wherein the arm is supported on and an integral extension of the sleeve and is tensed by deflecting it transverse to a longitudinal axis of the sleeve.

5. The device according to claim 3, wherein the arm is a an elongated element comprising an engaging means, which arm is deflected transverse to a longitudinal axis of the sleeve when the engaging means acts on a guiding area link inclined transverse to the longitudinal axis of the needle protecting sleeve, wherein the engaging means presses against the guiding area to elastically deflect and tense the arm and the force applied to the needle protecting sleeve by the deflected arm is a force component dependent on the inclination of the guiding area and points in an advancing direction of the needle protecting sleeve.

6. The device according to claim 5, wherein the force exerted directly by the arm converted, via the engagement between the engaging means and the guiding area, into an axial force which acts on the needle protecting sleeve.

7. The device according to claim 6, wherein the direct force of the deflected arm is transverse to the advancing direction of the needle protecting sleeve.

8. The device according to claim 3, wherein the needle protecting sleeve further comprises an engaging member which, when the needle protecting sleeve is in an initial position, is in an engagement with an abutment which acts in the distal direction and blocks a movement of the needle protecting sleeve in the distal direction and forms an end abutment.

9. The device according to claim 8, wherein the engaging member is spring-elastically arranged on a second arm, wherein the engaging member can be deflected by a second guiding area when the needle protecting sleeve is moved in the proximal direction, wherein when the needle protecting sleeve is in the position in which it has been moved in the proximal direction in relation to the initial position, the engaging member springs back out of its deflected position.

10. The device according to claim 9, wherein the engaging member is deflected by the second guiding area when the needle protecting sleeve is moved out of the needle protecting sleeve's retracted position in the distal direction, wherein the engaging member springs back out of the deflected position when the needle protecting sleeve is in the second extended position.

11. The device according to claim 10, wherein when the needle protecting sleeve is moved from the retracted position into the second extended position, the engaging member is arranged between an abutment which acts in the distal direction and blocks a movement of the needle protecting sleeve in the distal direction and an abutment which acts in the proximal direction and blocks a movement of the needle protecting sleeve in the proximal direction.

12. The device according to claim 11, wherein at least one of the abutments and/or at least part of the second guiding area is formed by a guiding track, wherein the guiding track is formed by the housing and the engaging member is cam-shaped and in the guiding track during all movements of the needle protecting sleeve.

13. The device according to claim 3, wherein the housing is a housing of an injection device or can be connected to the housing of an injection device.

14. An injection device comprising:
a) a housing with a longitudinal axis;
b) a product container formed or held by the housing, an unpreserved liquid drug being sterilely contained in the container;
c) a conveying means comprising a conveying member for delivering the drug; and
d) a protecting device for protecting against injuries from an injection needle associated with the injection device, said protecting device comprising a needle protecting sleeve which can be moved counter to a restoring force generated by deflection of an arm extending from the sleeve and generally parallel to the longitudinal axis that engages a guiding area of the housing to deflect the arm away from its orientation generally parallel to the longitudinal axis and generates the restoring force as the sleeve moves from a first extended position in which the sleeve extends distally beyond a distal end of the needle into a retracted position and is returned by the restoring force from the retracted position into a second extended position.

15. The injection device according to claim 14, wherein the arm is deflected by an engaging means of the arm pressed against a guiding area of the housing as the sleeve moves proximally.

16. The injection device according to claim 15, further comprising:
a) a dosing member which can perform a dosing movement relative to the housing to set a dose of the drug to be administered,
b) the conveying means comprising the conveying member for delivering the set dose,
c) wherein the dosing member is blocked in the direction of the dosing movement in a releasable dosing blocking engagement in an initial state of the injection device, and is free of the block at the end of a priming movement of the conveying member which serves to vent the container.

17. The injection device according to claim 16, used with an unpreserved drug or active agent.

18. The injection device according to claim 17, wherein the unpreserved drugs or active agents are at least one of: a drug based on FSH or an FSH variant, a neuroleptic drug, a vasodilative agent, a blood product, a drug for treating a rheumatic disease, an oncological drug, or a drug for treating an infectious disease.

19. The injection device of claim 14, wherein the arm comprises an arm that is integrally formed on, and protrudes from, the needle protecting sleeve, wherein the arm is adapted to flex transversely relative to a longitudinal axis of the needle protecting sleeve, and wherein when the needle protecting sleeve moves from the first extended position into the retracted position, the arm flexes transversely relative to the longitudinal axis to tense the arm, and when the needle protecting sleeve is in the retracted position, relaxation of the tensed spring arm applies a force that urges the needle protecting sleeve to the second extended position.

20. The injection device of claim 14, wherein the arm comprises an engaging means that acts on a portion of the guiding area that is inclined transverse to longitudinal axis of the needle protecting sleeve.

* * * * *